US011226344B2

(12) United States Patent
Kim et al.

(10) Patent No.: US 11,226,344 B2
(45) Date of Patent: Jan. 18, 2022

(54) MEASUREMENT METHOD FOR GLYCATED HEMOGLOBIN RATIO

(71) Applicant: GREEN CROSS MEDICAL SCIENCE, Yongin-si (KR)

(72) Inventors: Hyu Jeong Kim, Seoul (KR); Hyong Soo Kim, Yongin-si (KR); Dong Han Kim, Uiwang-si (KR); Eun Myung Shin, Suwon-si (KR); Jung Sub Shin, Ansan-si (KR); Soon Min Hong, Yongin-si (KR); Su Hyun Lee, Yongin-si (KR); Dong Cheol Choi, Yongin-si (KR)

(73) Assignee: GREEN CROSS MEDICAL SCIENCE, Yongin-si (KR)

( * ) Notice: Subject to any disclaimer, the term of this patent is extended or adjusted under 35 U.S.C. 154(b) by 273 days.

(21) Appl. No.: 16/343,941

(22) PCT Filed: Nov. 4, 2016

(86) PCT No.: PCT/KR2016/012652
§ 371 (c)(1),
(2) Date: Apr. 22, 2019

(87) PCT Pub. No.: WO2018/084337
PCT Pub. Date: May 11, 2018

(65) Prior Publication Data
US 2019/0242911 A1  Aug. 8, 2019

(51) Int. Cl.
*G01N 33/72* (2006.01)
*G01N 33/66* (2006.01)
*G01N 35/00* (2006.01)

(52) U.S. Cl.
CPC ........... *G01N 33/723* (2013.01); *G01N 33/72* (2013.01); *G01N 33/726* (2013.01); *G01N 35/00* (2013.01); *G01N 33/66* (2013.01)

(58) Field of Classification Search
CPC ...... G01N 33/66; G01N 33/72; G01N 33/721; G01N 33/723; G01N 33/726; G01N 35/00;
(Continued)

(56) References Cited

U.S. PATENT DOCUMENTS

| 5,162,237 A | 11/1992 | Messenger et al. |
| 5,372,948 A | 12/1994 | Yip |

(Continued)

FOREIGN PATENT DOCUMENTS

| CN | 104897907 A | 9/2015 |
| CN | 105021544 A | 11/2015 |

(Continued)

OTHER PUBLICATIONS

International Search Report for PCT/KR2016/012652, dated Jul. 24, 2017.
(Continued)

*Primary Examiner* — Maureen Wallenhorst
(74) *Attorney, Agent, or Firm* — Sughrue Mion, PLLC

(57) ABSTRACT

Disclosed is a measurement method for a glycated hemoglobin ratio. According to a measurement method for a glycated hemoglobin ratio of the present invention, reagents are easy and convenient to use because of their sequential leakage during the rotation of a cassette, are all discharged by the rotation with no remaining reagent, and are not mixed with each other. Therefore, measurement results are accurate, with fewer errors in the quantities of used reagents and sample blood.

9 Claims, 12 Drawing Sheets

(58) Field of Classification Search
CPC ........... Y10T 436/25; Y10T 436/25375; Y10T 436/255; Y10T 436/2575
USPC ......... 436/43, 45, 63, 66, 67, 164, 165, 174, 436/177, 178, 180; 422/63, 64, 82.05, 422/82.09, 503, 506, 533, 548, 554; 435/7.1

See application file for complete search history.

(56) References Cited

U.S. PATENT DOCUMENTS

| | | | |
|---|---|---|---|
| 6,300,142 | B1 | 10/2001 | Andrewes et al. |
| 8,557,590 | B2* | 10/2013 | Bae .................... G01N 33/723 |
| | | | 436/67 |
| 2007/0154351 | A1* | 7/2007 | Bae ......................... C12Q 1/60 |
| | | | 422/400 |
| 2009/0093012 | A1 | 4/2009 | Bae et al. |
| 2010/0196999 | A1 | 8/2010 | Bae et al. |
| 2011/0104731 | A1 | 5/2011 | Teng et al. |
| 2013/0121898 | A1 | 5/2013 | Chen et al. |
| 2014/0127828 | A1 | 5/2014 | Hou et al. |
| 2015/0044764 | A1 | 2/2015 | Cha et al. |
| 2015/0147804 | A1 | 5/2015 | Cha et al. |
| 2016/0266099 | A1 | 9/2016 | Price et al. |
| 2018/0193841 | A1* | 7/2018 | Liu .................. G01N 33/54366 |
| 2019/0234981 | A1* | 8/2019 | Kim .................... G01N 33/726 |

FOREIGN PATENT DOCUMENTS

| | | |
|---|---|---|
| EP | 0 407 827 A2 | 1/1991 |
| EP | 2047909 A2 | 4/2009 |
| EP | 2047909 A3 | 8/2009 |
| EP | 3521830 A1 | 8/2019 |
| JP | 3447360 B2 | 9/2003 |
| JP | 2009-300433 A | 12/2009 |
| JP | 2015-524566 A | 8/2015 |
| KR | 10-0798471 B1 | 1/2008 |
| KR | 10-0799354 B1 | 1/2008 |
| KR | 10-2010-0136744 A | 12/2010 |
| KR | 10-1069823 B1 | 10/2011 |
| KR | 10-2013-0119742 A | 11/2013 |

OTHER PUBLICATIONS

International Search Report dated Jun. 26, 2017 in International Application No. PCT/KR2016/010875 Translation.

* cited by examiner

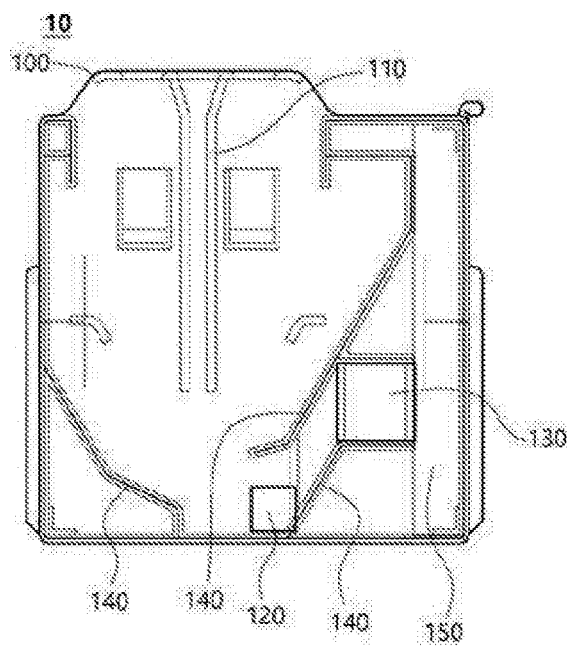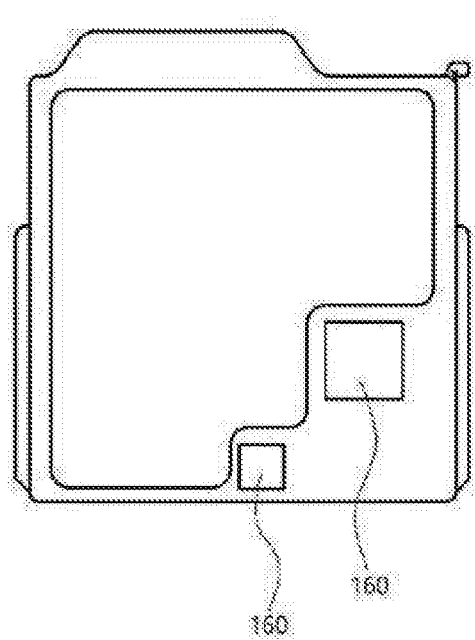
Fig. 3 (a)    Fig. 3 (b)

[Fig. 6]
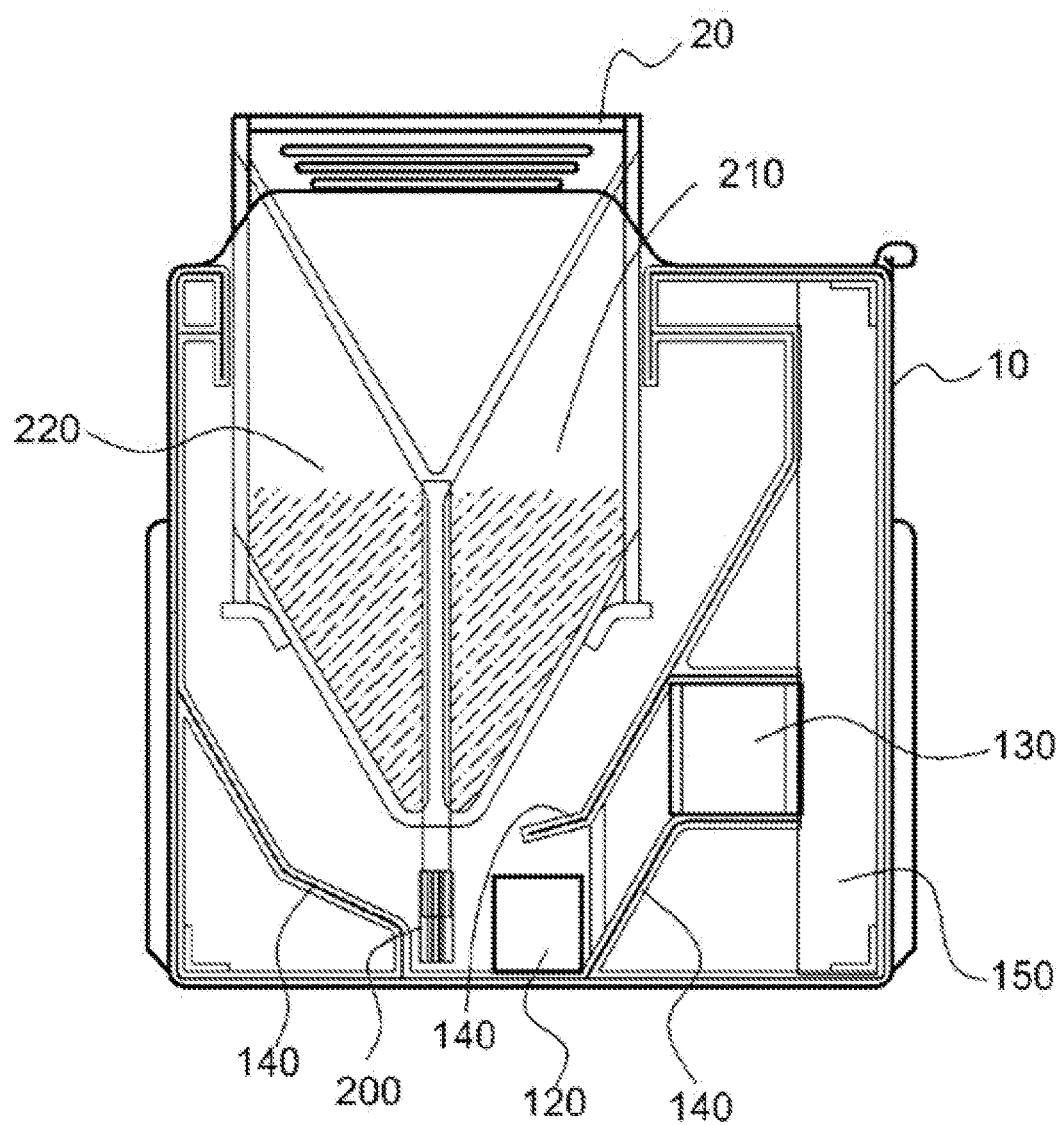

[Fig. 7]
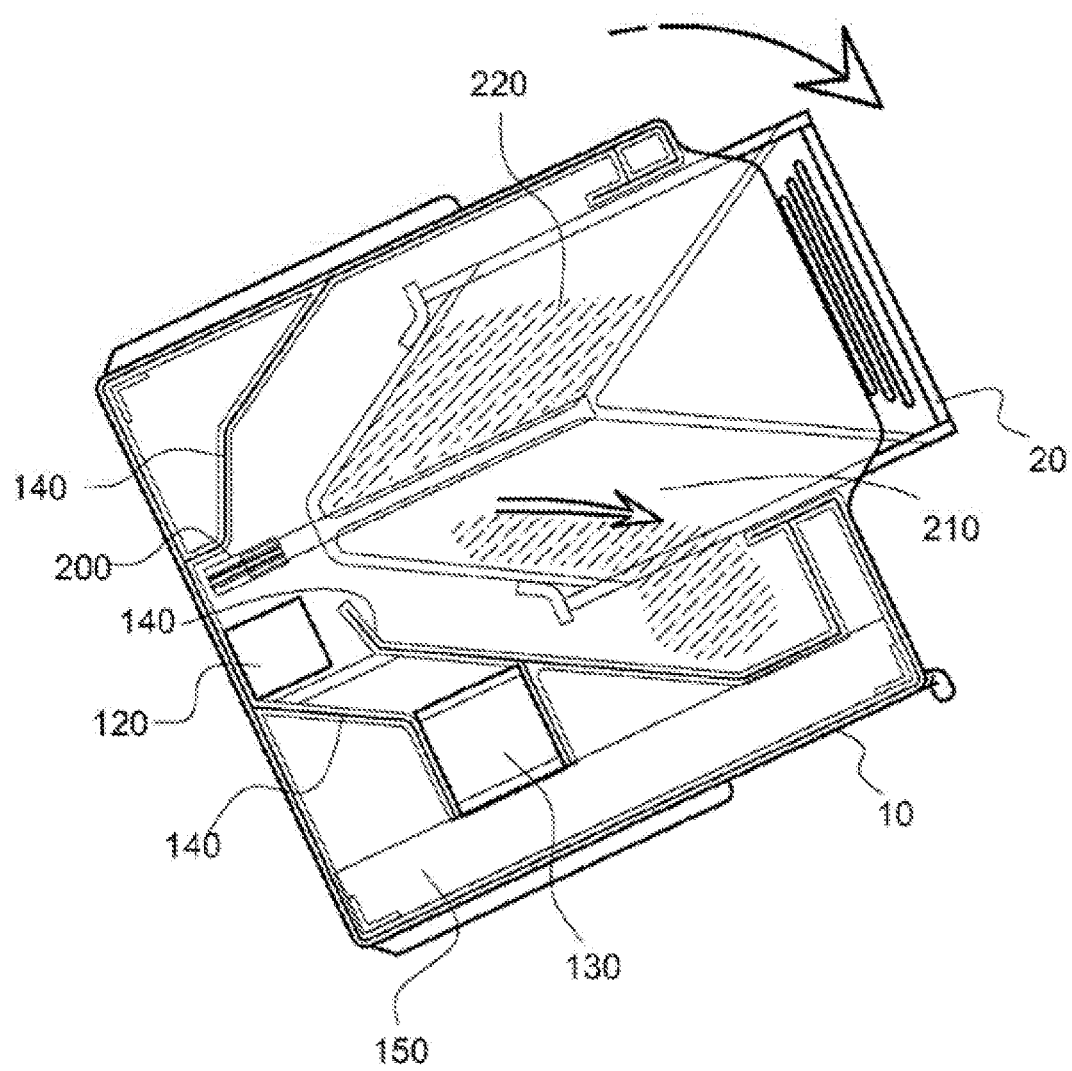

【Fig. 8】
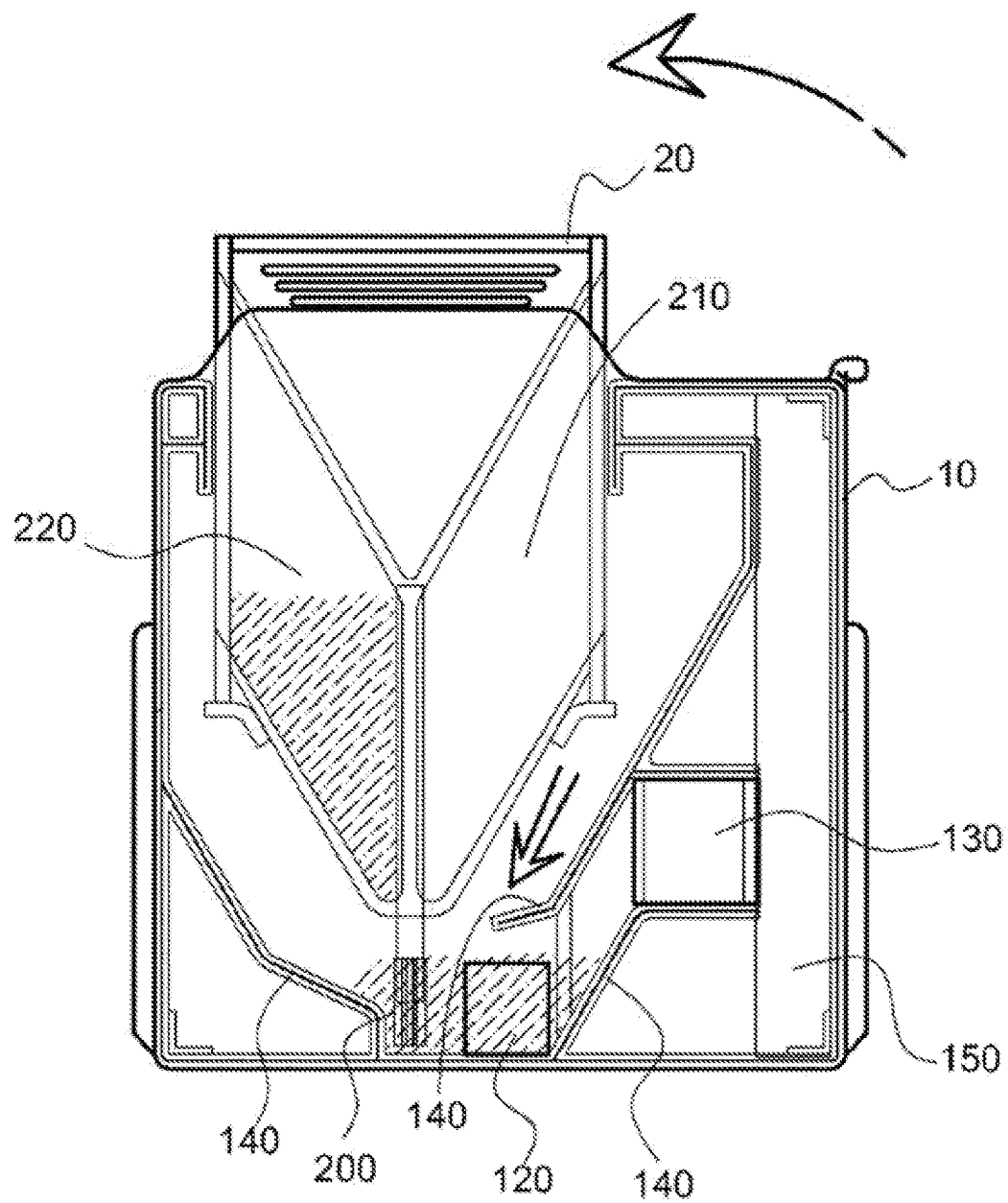

[Fig. 9]
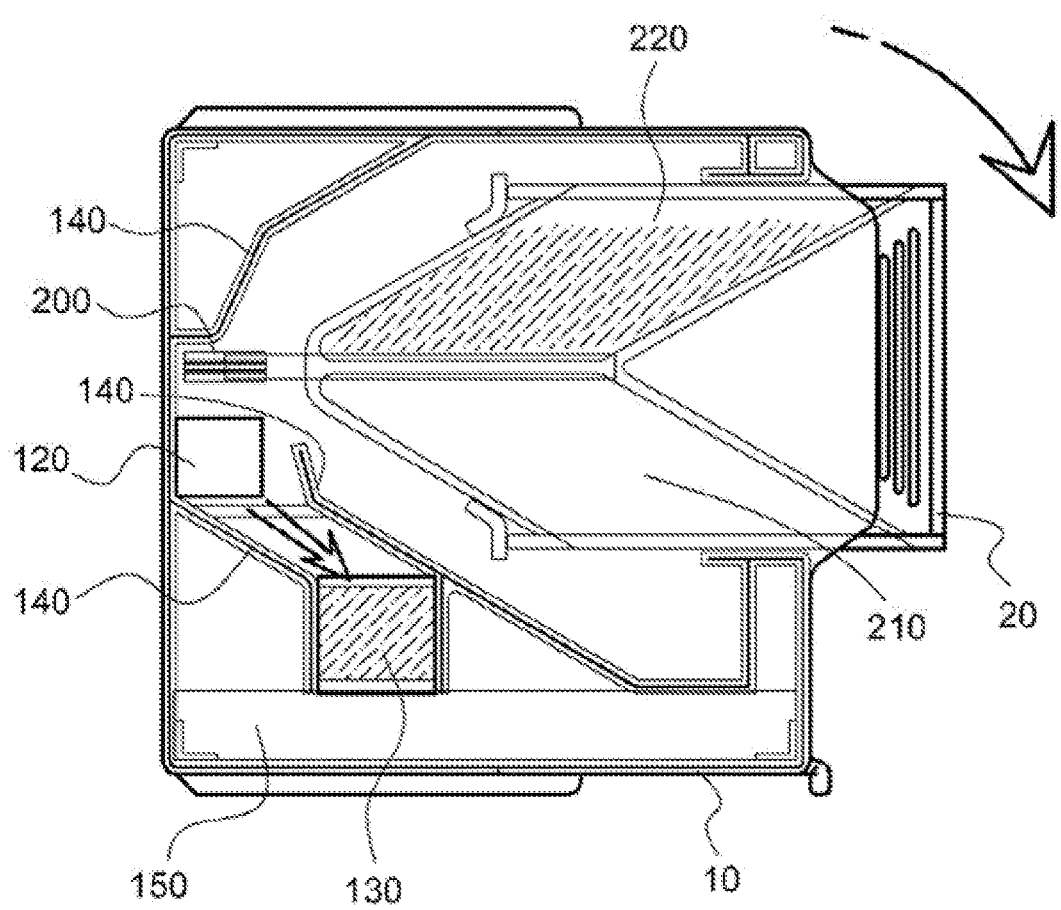

【Fig 10】
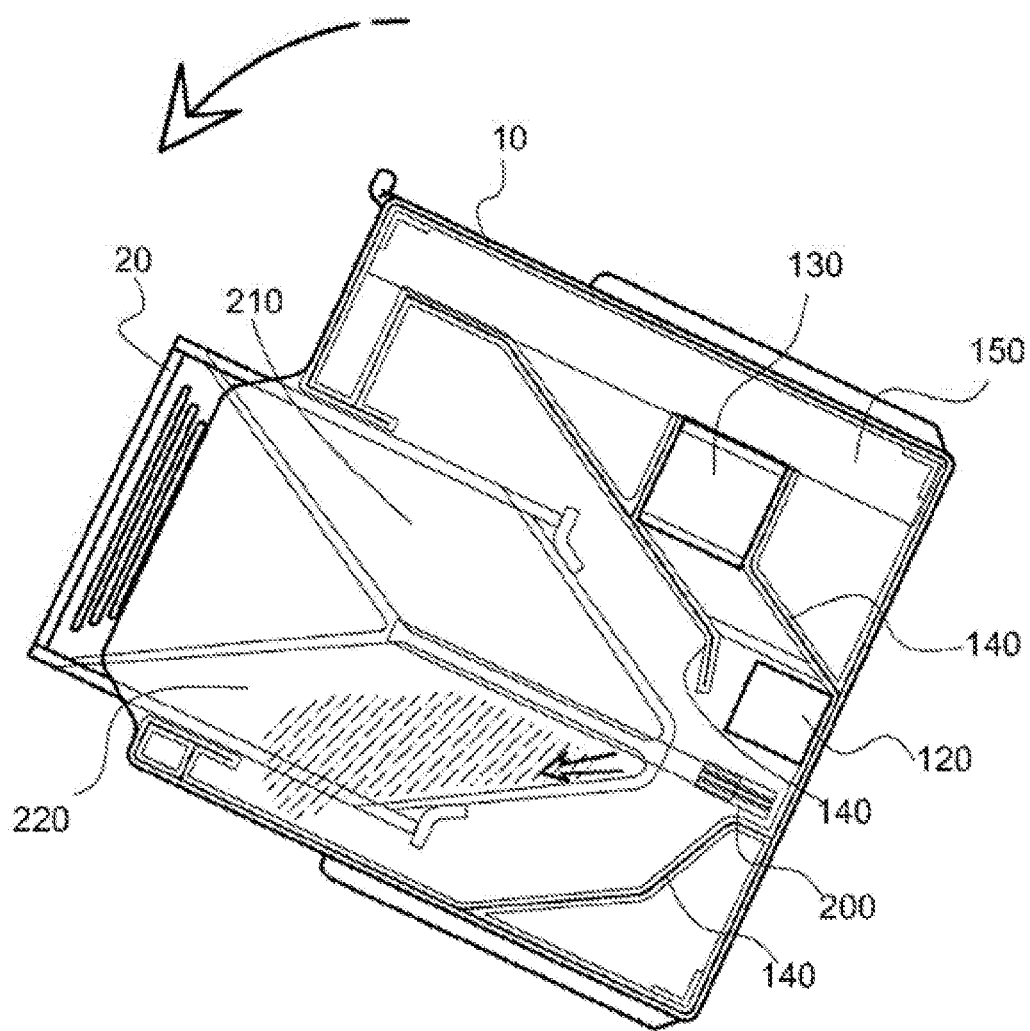

【Fig 11】
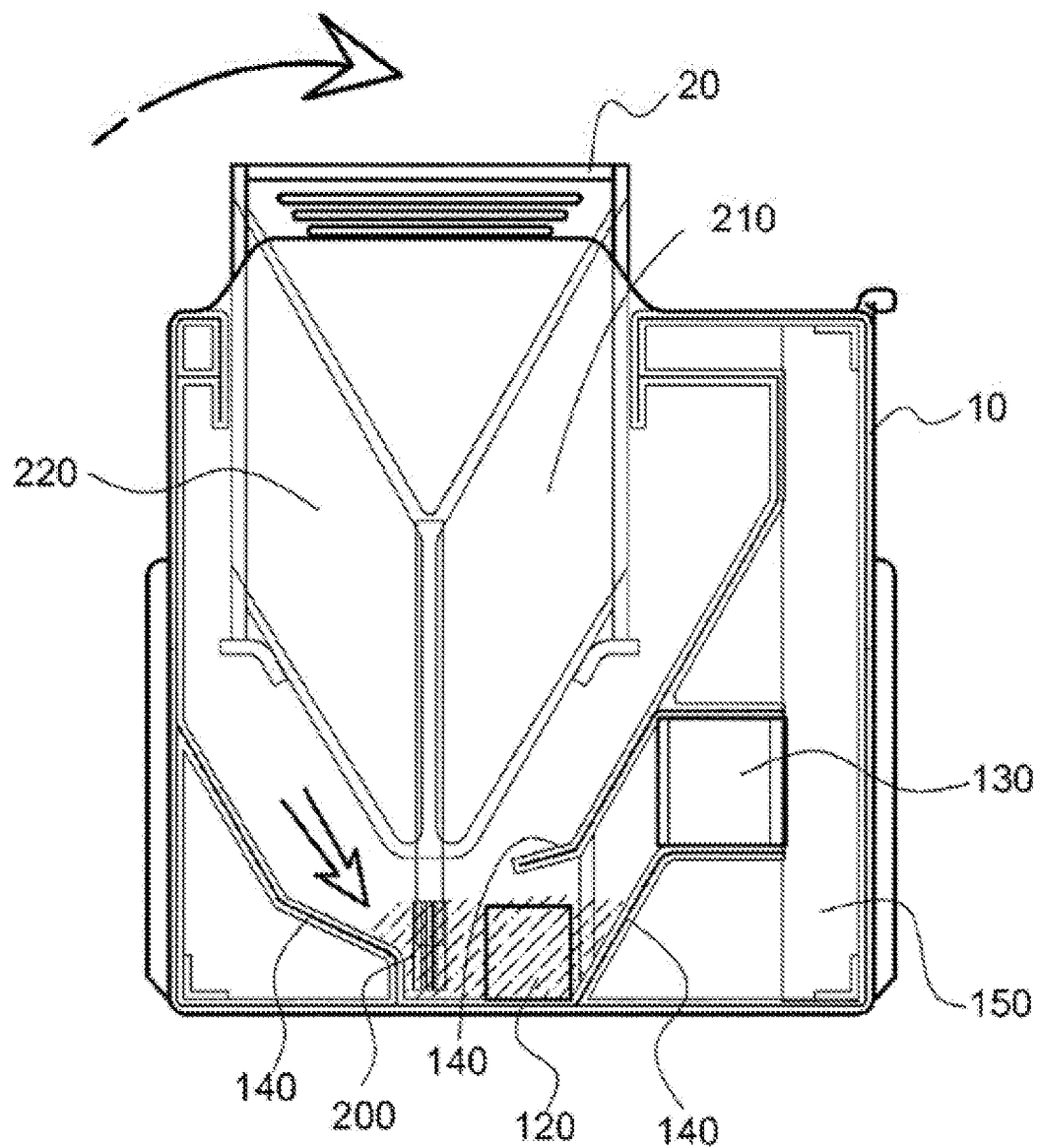

[Fig. 12]
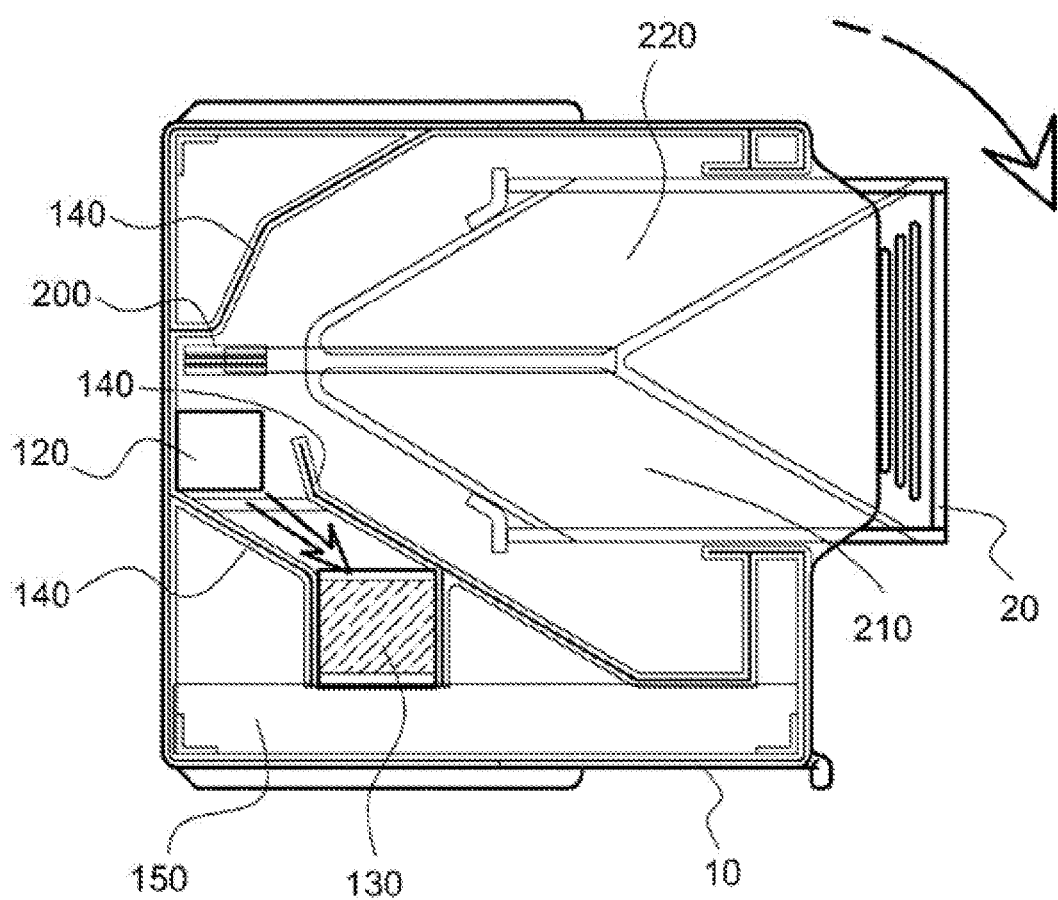

MEASUREMENT METHOD FOR GLYCATED HEMOGLOBIN RATIO

This Application is a National Stage of Application No. PCT/KR2016/012652 filed Nov. 4, 2016.

TECHNICAL FIELD

The present invention relates to a method for measuring glycated hemoglobin ratio.

BACKGROUND ART

In the fields of medical diagnosis or drug-based therapy, the concentration measurement of analytes of anesthetics or harmful chemicals has recently been useful in medical or environmental fields. Above all, the concentration measurement of biological samples used in the fields of medical diagnosis and therapy is increasingly drawing interest along with an increase in human desire to be free from various diseases. Particularly, with regard to diabetes, the glycated hemoglobin test capable of measuring blood sugar allows a relatively long-term average value of the blood sugar to be detected by one-time measurement, and thus has an increasing interest.

Hemoglobin A1c (HbA1c) is also called glycated hemoglobin, and is present in human red blood cells as a part of hemoglobin. When a concentration of blood sugar (glucose) in the blood rises, a glucose moiety in the blood binds to hemoglobin. This hemoglobin conjugated with glucose is referred to as glycated hemoglobin. Blood sugar levels can be determined by this glycated hemoglobin test, which has an advantage in that it can be conducted by collecting blood regardless of the meal time.

Meanwhile, U.S. Pat. No. 6,300,142 discloses an apparatus for reacting a test sample with a first reactant in a first inlet port and sequentially reacting the reacted test sample with a second reactant in a second inlet port to measure the analyte present in the test sample. In this case, the measurement of the analyte has to be conducted periodically and sequentially. Further, a user has to intervene in the measuring process in such a manner that he or she injects the test sample sequentially to react the test sample with other materials. Furthermore, since beads conjugated with the glycated hemoglobin have to be filtered once, the measuring process is complicated and takes a long time. That is, since the conventional measuring process requires the user's direct intervention in various processing steps, the user may feel inconvenient. Also, the user's direct intervention makes the measuring process more complicated, thereby further increasing the measuring time.

Therefore, there is a demand for research on the method for measuring glycated hemoglobin ratio, which is easy to measure and can provide accurate measurement results.

PRIOR ART DOCUMENTS

Patent Documents

Korean Patent No. 10-1069823, entitled "cassette for measuring the concentration of glycosylated hemoglobin."
Korean Patent No. 10-0799354, entitled "reagent vessel."

DISCLOSURE

Technical Problem

The present inventors have completed the present invention based on the idea that when glycated hemoglobin ratio is measured using a cassette for measuring glycated hemoglobin ratio, the reagents automatically leak out sequentially in the course of the rotation of the cassette, so that it is easy to use and the reagents are fully discharged without any residual reagents by the rotation, thereby outputting the accurate measurement results.

Accordingly, it is an object of the present invention to provide a method which can more effectively measure glycated hemoglobin ratio by inducing each reagent to leak sequentially in accordance with the rotation of the cassette.

Technical Solution

In order to achieve the above purpose, the present invention provides a method for measuring glycated hemoglobin ratio using a cassette used in a device for measuring glycated hemoglobin ratio, wherein the cassette comprises: a cartridge which includes a first storage zone for storing a first reagent, a second storage zone for storing a second reagent, and a blood sampling unit capable of injecting a blood sample into the cassette, and is inserted into the cassette; a first measurement zone in which the blood sample reacts with the first reagent to measure an amount of total hemoglobin; and a second measurement zone in which the reacted blood sample reacts with the second reagent to measure an amount of glycated hemoglobin, wherein as the cassette rotates by a predetermined angle or more, the first reagent or the second reagent leaks from the first storage zone or the second storage zone, or moves into the first measurement zone or the second measurement zone, and wherein the method comprises the steps of:
a) rotating the cassette in a first direction to leak the first reagent from the first storage zone;
b) rotating the cassette in a second direction to react the first reagent with the blood sample in the first measurement zone and measuring an amount of total hemoglobin;
c) rotating the cassette in the first direction to move a blood sample mixture formed by reacting the first reagent with the blood sample to the second measurement zone;
d) rotating the cassette in the second direction to leak the second reagent from the second storage zone;
e) rotating the cassette in the first direction to move the leaked second reagent to the second measurement zone and washing the blood sample mixture with the second reagent to measure an amount of glycated hemoglobin; and
f) dividing the measured amount of glycated hemoglobin by the measured amount of total hemoglobin to calculate glycated hemoglobin ratio in the blood sample.

In an embodiment of the present invention, the method may further comprise, prior to step a), the steps of:
1) identifying the information of the cassette; and
2) confirming whether a first reagent and a second reagent are present in the cassette.

In an embodiment of the present invention, the first reagent includes a hemolysate and a glycated hemoglobin binding material-bead which selectively reacts with the glycated hemoglobin, wherein the bead may include one or more selected from the group consisting of an agarose bead, a sepharose bead, a latex bead, a glass bead, and a magnetic bead.

In an embodiment of the present invention, the glycated hemoglobin binding material may include one or more selected from the group consisting of a boronic acid, concanavalin A, and an antibody.

In an embodiment of the present invention, the cassette may rotate 60-130° in the first direction in step a), rotates 60-130° in the second direction in step b), rotates 60-130° in the first direction in step c), rotates 150-240° in the second direction in step d), and rotates 150-220° in the first direction in step e).

In an embodiment of the present invention, the second reagent may not leak from the second storage zone in steps a) to c).

In an embodiment of the present invention, step b) may comprise the step of shaking the cassette to facilitate the reaction of the blood sample with the first reagent.

In an embodiment of the present invention, step b) may comprise the step of measuring the amount of total hemoglobin in the blood sample by the optical reflectometry technique through the optical sensor.

In an embodiment of the present invention, step e) may comprise the steps of:

e1) rotating the cassette in the first direction to move second reagent to the second measurement zone; and e2) washing the blood sample mixture with the second reagent moved to the second measurement zone to remove non-specific hemoglobin and measuring the amount of glycated hemoglobin in the blood sample.

In an embodiment of the present invention, step e) may comprise the step of measuring the amount of glycated hemoglobin in the blood sample by the optical reflectometry technique through the optical sensor.

Advantageous Effects

The method for measuring glycated hemoglobin ratio according to the present invention is easy to use since the reagents leak out sequentially during the rotation of the cassette, the reagents are fully discharged without any residual reagents by the rotation, and the reagents do not mix with each other. Therefore, the measurement results are accurate because there is little error in the amount of the reagents used and the amount of blood samples.

DESCRIPTION OF DRAWINGS

FIG. 3 (a) and FIG. 3(b) illustrate an external appearance and an internal appearance according to an embodiment of the cassette used in the method of the present invention.

FIGS. 6 to 12 are exemplary views showing the process in which the cassette used in the method of the present invention rotates to measure the glycated hemoglobin ratio.

BEST MODE

Figure 1:
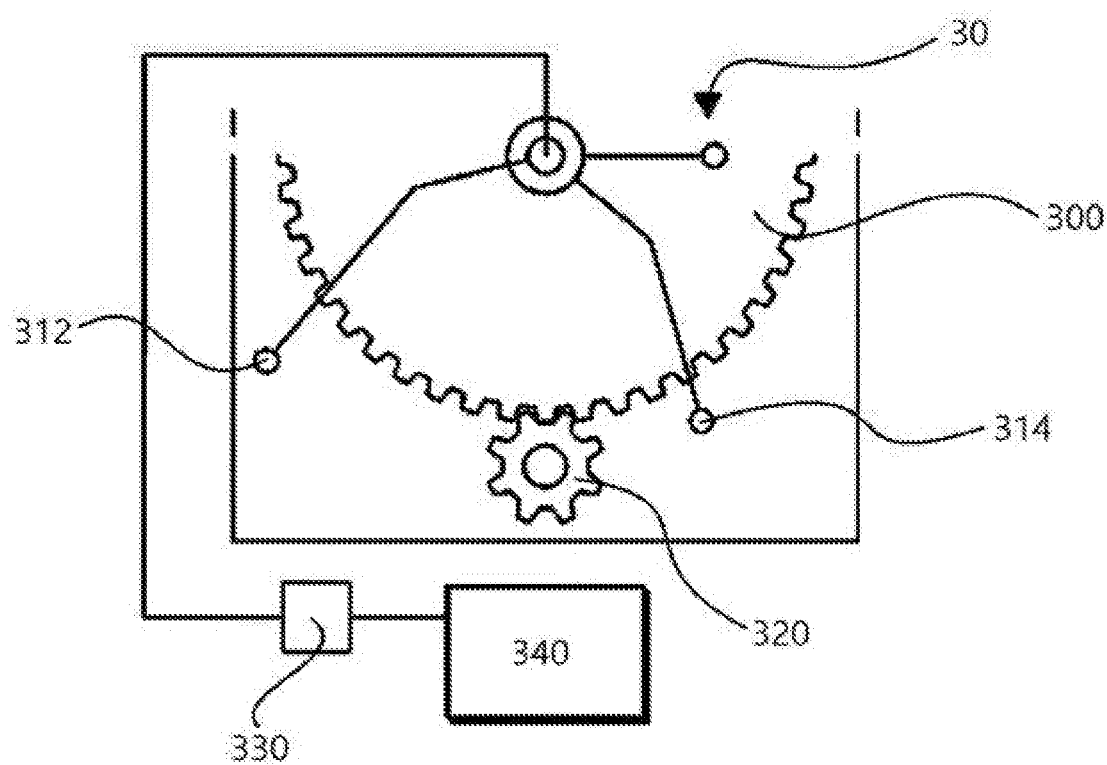
FIG. 1 is a schematic view showing an exemplary device for measuring glycated hemoglobin ratio in which a separable cassette for measuring glycated hemoglobin ratio used in the method of the present invention can be used.

Hereinafter, preferred examples according to the present invention will be described in detail with reference to the accompanying drawings. However, the present invention is not limited to the examples described herein and may be embodied in other forms.

As used herein, terms "rotation in a first direction" and "rotation in a second direction" refer to rotation in mutually opposite directions. For example, if the first direction is clockwise, then the second direction automatically means counterclockwise, or vice versa.

The term "original state of the cassette" means that the cassette stands upright on a flat ground without rotation or tilt, and may include a state of tilting about −35 to 30° relative to the ground depending on the shape of the cartridge.

In addition, the cassette used in the method of the present invention has a form in which the cartridge and the cassette are separated before the measurement of the glycated hemoglobin ratio. In the measurement of glycated hemoglobin ratio, the measurement is performed while the cartridge is inserted into the cassette including the first reagent, the second reagent, and the blood sample.

The present invention provides a method for measuring glycated hemoglobin ratio using a cassette used in a device for measuring glycated hemoglobin ratio, wherein the cassette 10 comprises: a cartridge 20 which includes a first storage zone 210 for storing a first reagent, a second storage zone 220 for storing a second reagent, and a blood sampling unit 200 capable of injecting a blood sample into the cassette 10, and is inserted into the cassette 10; a first measurement zone 120 in which the blood sample reacts with the first reagent to measure an amount of total hemoglobin; and a second measurement zone 130 in which the reacted blood sample reacts with the second reagent to measure an amount of glycated hemoglobin, wherein as the cassette 10 rotates by a predetermined angle or more, the first reagent or the second reagent leaks from the first storage zone 210 or the second storage zone 220, or moves into the first measurement zone 120 or the second measurement zone 130, and the method comprises the steps of:

a) rotating the cassette 10 in a first direction to leak the first reagent from the first storage zone 210;

b) rotating the cassette 10 in a second direction to react the first reagent with the blood sample in the first measurement zone 120 and measuring an amount of total hemoglobin;

c) rotating the cassette 10 in the first direction to move a blood sample mixture formed by reacting the first reagent with the blood sample to the second measurement zone 130;

d) rotating the cassette 10 in the second direction to leak the second reagent from the second storage zone 220;

e) rotating the cassette 10 in the first direction to move the leaked second reagent to the second measurement zone 130 and washing the blood sample mixture with the second reagent to measure an amount of glycated hemoglobin; and f) dividing the measured amount of glycated hemoglobin by the measured amount of total hemoglobin to calculate glycated hemoglobin ratio in the blood sample.

In an embodiment of the present invention, the method may further comprise, prior to step a), the steps of:

1) identifying the information of the cassette; and 2) confirming whether a first reagent and a second reagent are present in the cassette.

First, an exemplary device for measuring glycated hemoglobin ratio 30 which may be used in the method for measuring glycated hemoglobin ratio according to the present invention will be described with reference to FIG. 1.

Referring to FIG. 1, the cassette 10 in which the cartridge 20 is inserted into a device for measuring glycated hemoglobin ratio 30. At this time, the device for measuring glycated hemoglobin ratio 30 may rotate the cassette 10 clockwise or counterclockwise according to a certain pattern. The rotation of the cassette 10 causes the first reagent or the second reagent to leak sequentially into the cassette 10, respectively, to be stirred together with the blood sample, and to move into the first measurement zone 120 or the second measurement zone 130 so that the measurement can be performed. The device for measuring glycated hemoglobin ratio 30 can measure the amount of glycated hemoglobin using an optical reflectometry technique.

For example, when the amount of glycated hemoglobin in a blood sample is measured, a characteristic that hemoglobin specifically absorbs an optical signal of a specific frequency is utilized. At this time, it is preferable that the device for measuring glycated hemoglobin ratio 30 measures the amount of glycated hemoglobin using a light-receiving element and a light-emitting element such as a photo diode.

Referring to FIG. 1, the device for measuring glycated hemoglobin ratio 30 may comprise a cassette 10 accommodation part 300, a cassette 10 check sensor 312, a measurement sensor 314, a driving unit 320, a signal conversion unit 330, and a controller 340.

The cassette 10 accommodation part 300 has a space into which the cassette 10 is inserted. It is preferable that the cassette 10 accommodation part 300 has a sufficient space so that the cassette 10 may rotate clockwise or counterclockwise without any interruption therein.

The cassette 10 check sensor 312 may confirm whether the solution containing the reagent such as the first reagent and the second reagent in the cassette 10 is properly present in the first storage zone 210 and the second storage zone 220. The cassette check sensor 312 confirms detection of reagents by an absorption photometry method using an optical sensor that emits an optical signal by a light-emitting element and receives the optical signal that has passed through the cassette 10 by a light-receiving element. That is, the cassette 10 check sensor 312 outputs a light-emitting control signal to the light-emitting element and converts an optical signal received from the light-receiving element into an electrical signal, thereby being able to detect whether the first reagent and second reagent are properly present.

In other words, the light-emitting element emits an optical signal having a specific wavelength. For example, when the amount of glycated hemoglobin is to be measured, the hemoglobin of the blood sample may emit an optical signal having a wavelength of about 400-600 nm which specifically shows absorption. The light-receiving element receives an optical signal which is emitted from the light-emitting element and passes through the cassette 10.

The measurement sensor 314 measures the amount of total hemoglobin and the amount of glycated hemoglobin which are contained in the second measurement zone 130 of the cassette 10. At this time, by outputting a light-emitting control signal to the light-emitting element and converting an optical signal inputted from the light-receiving element into an electrical signal, the amount of total hemoglobin and the amount of glycated hemoglobin which are contained in the cassette 10 can be measured.

The driving unit 320 applies an external power to the cassette 10. For example, the driving unit 320 may be a motor. The cassette 10 may rotate according to a predetermined rule by the external power, and the rotation angle may freely be selected from −270° to 270°.

The signal conversion unit 330 is a general Analog-to-Digital (A/D) converter.

The controller 340 controls the entire system, and is preferably embodied as a microprocessor into which a ROM, a RAM, and peripheral devices are integrated. The controller 340 can identify the cassette 10, detect the injection of a sample solution, or measure the amount of glycated hemoglobin.

That is, the controller 340 outputs a light-emitting control signal to the light-emitting element and converts an optical signal inputted from the light-receiving element into an electrical signal through A/D converter, thereby detecting whether the first reagent and the second reagent are properly present in the cassette 10. In this manner, it is possible to measure the amount of glycated hemoglobin included in the second measurement zone 130 of the cassette 10.

Next, the cassette 10 which can be used in the method for measuring glycated hemoglobin ratio according to the present invention will be described with reference to FIG. 3.

The first storage zone 210 and the second storage zone 220 may each store at least one reagent.

The first storage zone 210 may store the first reagent. Wherein the first reagent can react with the blood sample. For example, the first reagent may include a hemolysate for hemolyzing the blood sample and a glycated hemoglobin binding material-bead which selectively reacts with the glycated hemoglobin.

The hemolysate may be, for example, a buffer solution containing a surfactant, such as N-2-Hydroxyethylpiperazine-N'-2-ethanesulfonic Acid (HEPES; pH 8.1). The blood sample hemolyzed by the hemolysate may include a non-glycated hemoglobin and a glycated hemoglobin.

The glycated hemoglobin binding material may be a material capable of specifically binding to the glycated hemoglobin. For example, the glycated hemoglobin binding material may include one or more selected from the group consisting of a boronic acid (BA), concanavalin A (lectin), and an antibody.

The bead may include one or more selected from the group consisting of a polymer polysaccharide support such as agarose, cellulose, or sepharose; a latex bead such as polystyrene, polymethylmethacrylate, or polyvinyltolune; a glass bead; and a magnetic bead.

It is preferable that the particle diameter of the glycated hemoglobin binding material-bead is selected in consideration with the precipitation time of the glycated hemoglobin binding material-bead conjugated with glycated hemoglobin after reaction, and the reactivity with the glycated hemoglobin.

In summary, the first reagent may include the hemolysate for hemolyzing the blood sample and the glycated hemoglobin binding material-bead which selectively reacts with the glycated hemoglobin. The first reagent hemolyzes the blood sample, and then the amount of total hemoglobin is measured after about 10-20 seconds and the reaction of the first reagent and the glycated hemoglobin is performed for about 30-100 seconds.

The second storage zone 220 may store the second reagent. The second reagent may be a reagent including a washing solution which is able to wash off a mixture of the first reagent and the blood sample.

Most of hemoglobin (Hb) present in red blood cells of a blood sample is non-glycated hemoglobin ($A_o$). Only 4-15% of the non-glycated hemoglobin reacts with glucose to become glycated hemoglobin (HbA1c). Accordingly, the glycated hemoglobin binding material-beads in the first reagent which has reacted with the blood sample include non-glycated hemoglobin as well as glycated hemoglobin. Therefore, in order to measure only the glycated hemoglobin in the blood sample, it is needed to remove the non-glycated hemoglobin from the glycated hemoglobin binding material-beads. To this end, it is preferable that the second reagent includes a washing solution which is able to wash off the non-glycated hemoglobin to enable the measurement of glycated hemoglobin.

As the cassette 10 rotates by a predetermined angle or more, the first reagent or the second reagent leaks from the first storage zone 210 or the second storage zone 220, or moves into the first measurement zone 120 or the second measurement zone 130. If the cassette 10 does not rotate in the direction and angle at which the first reagent or the second reagent can leak in steps a) and d), the first reagent or the second reagent may not leak from the first storage zone 210 or the second storage zone 220.

The first storage zone 210 and the second storage zone 220 may be formed such that the first reagent or the second reagent does not leak out until the cassette 10 rotates by more than a predetermined angle. According to the cassette 10 used in the method of the present invention, even if the cartridge 20 comprising the first storage zone 210 and the second storage zone 220 is inserted into the cassette 10, the first reagent and the second reagent do not leak out in the original state in which the cassette 10 does not rotate. The first reagent or the second reagent may leak out sequentially only when the cassette 10 into which the cartridge 20 is inserted rotates by a predetermined angle or more. Therefore, a leakage hole, which is a passage through which the reagent leaks out, may be formed on the upper side of the first storage zone 210 and the second storage zone 220. Also, each of leakage holes may be formed on the upper end of each storage zone in the opposite direction to each other so that as the cassette 10 rotates in the opposite direction, the first reagent and the second reagent may independently leak out.

The blood sample, the first reagent, and the second reagent, which have leaked into the cassette 10 according to the rotation of the cassette 10, may also move independently from the cassette 10 to the measurement zone in accordance with the rotation of the cassette 10.

The first measurement zone 120 is a region in which the blood sample and the first reagent react and simultaneously measures the amount of total hemoglobin in the blood sample reacted with the first reagent. In the first measurement zone 120, the amount of total hemoglobin in the blood sample can be measured by an optical reflectometry technique. For example, the optical reflectometry technique utilizes the characteristic that hemoglobin specifically absorbs an optical signal of a specific frequency. The concentration of total hemoglobin can be measured by relatively measuring the intensity or tone of light by the characteristic of hemoglobin.

The second measurement zone 130 is a region into which after the blood sample are mixed with the first reagent and the amount of total hemoglobin is measured in the first measurement zone 120, the blood sample mixture that has reacted with the first reagent moves in accordance with the rotation of the cassette 10, as well as a region in which the blood sample mixture reacts with the second reagent and the amount of glycated hemoglobin is measured. The measurement principle may be the same as that of the first measurement region 120. Here, the term "reaction" refers to a comprehensive reaction including not only a chemical reaction but also washing, bonding, agitation, etc.

The blood sampling unit 200 collects and contains a blood sample and injects the blood sample into the cassette 10, and may be in the form of a capillary.

It is so that the blood sample to be measured is suck by the form of a capillary of the blood sampling unit 200. Particularly, the inside diameter of the tip of the blood sampling unit 200 is smaller than that of the remaining portion so that the capillary phenomenon is easily generated.

On the other hand, when the blood sample is injected into the cassette 10 from the blood sampling unit 200, if the amount of the blood sample to be sampled is not constant or exceeds the measurement limit amount, it may lead to an error in the result value. If an excessive amount of blood is contained in the blood sampling unit 200, the measuring device may deviate from the measurable range to provide an excessive value. In the case of, for example, Clover A1c, available from Infopia Co., Inc., a measurable total hemoglobin level is 7-20 g/dl, and if excess blood is injected, the device recognizes that the hemoglobin level is out of the measurable range, thereby resulting in displaying a measured value higher than the normal value.

Therefore, the form of the blood sampling unit 200 is important. The tip of the blood sampling unit 200 includes a gap formed in parallel to the center, the width of the tip is narrowed toward the end of the tip, and the gap formed inside may form a groove close to the curve.

The amount of blood required for the measurement is preferably about 2.5-5.5 ul. The blood sampling unit 200 according to the present invention may contain about 3 ul of blood and its specific form prevents the excessive blood from sticking together to the blood sampling unit 200.

The cassette 10 may further comprise an insertion guide unit 110 for guiding an insertion direction when the cartridge 20 is inserted into the cassette 10.

The first storage zone 210 is preferably inserted into the cassette 10 so as to be closer to the first measurement zone 120 and the second measurement zone 130 than the second storage zone 220. The insertion guide unit 110 may be a concavo-convex shape formed on the inner surface of the cassette 10, preferably the cartridge 20 can be inserted into the cassette 10 only in one direction by the insertion guide unit 110, but is limited thereto.

The cartridge 20 further comprises a leakage preventing unit 230 which is disposed at one end of the first storage zone 210 and the second storage zone 220, respectively, to prevent the first reagent and the second reagent from leaking out, and can be removed from the cartridge 20 when the cartridge 20 is inserted into the cassette 10.

The leakage preventing unit 230 may be formed at one end, preferably the upper side, of the first storage zone 210 and the second storage zone 220, respectively, and may seal the first reagent and the second reagent stored in the storage zones from the outside. The leakage preventing unit 230 may be caught and removed or damaged by the removing part 100 when the cartridge 20 is inserted into the cassette 10. The leakage preventing unit 230 may be a foil cover or a foil tab and may be a member that is not corroded or damaged from the reagent.

The leakage preventing unit 230 is removed by the removing part 100 which is disposed in the inlet port of the cassette 10 and may have a protruding part so that the leakage preventing unit 230 can be caught and removed.

The leakage preventing unit 230 is automatically removed by the removing part 100 when the cartridge 20 is inserted into the cassette 10, and the removing part 100 may have a suitable protruding shape so that the leakage preventing unit 230 can be caught and removed.

The first reagent may leak from the first storage zone 210 when the cassette 10 is rotated 60-130° in the first direction based on the original state.

The second reagent may leak from the second storage zone 220 when the cassette 10 is rotated 60-130° in the second direction based on the original state.

The rotation in the first direction and the rotation in the second direction mean rotation in mutually opposite directions. Even if the leakage preventing unit 230 is removed, the first reagent or the second reagent may not leak until the cassette 10 rotates. When the cassette 10 rotates 60-130° in the first direction or the second direction after the leakage preventing unit 230 is removed, the first reagent or the second reagent may leak through the leakage holes formed on the upper side of each storage zone. For example, when the cassette 10 rotates 60-130° in the first direction, only the first reagent may leak, but the second reagent does not leak. Conversely, when the cassette 10 rotates 60-130° in the second direction, only the second reagent may leak, but the first reagent does not leak.

The cassette 10 may further comprise a delivery guide unit 140 for guiding for the blood sample, the first reagent, or the second reagent, to move to the first measurement zone 120 or the second measurement zone 130.

The delivery guide unit 140 is a concavo-convex shape formed inside the cassette 10 and guides so that according to the rotation of the cassette 10, the first reagent leaking from the first storage zone 210 may move to the first measurement zone 120, a mixture of the blood sample and the first reagent from the first measurement zone 120 may move to the second measurement zone 130, and the second reagent leaking from the second storage zone 220 may move to the second measurement zone 130.

The cassette 10 may further comprise a sample absorption unit 150 which is located at one end of the second measurement zone 130 to absorb the measured blood sample and the sample. The sample absorption unit 150 absorbs the measured blood sample mixture to prevent the blood sample mixture from leaking out. For example, in order to measure the amount of glycated hemoglobin, the sample absorption unit 150 may absorb non-glycated hemoglobin and the remaining materials except for the glycated hemoglobin binding material-bead conjugated with glycated hemoglobin, present in the second measurement zone 130. The sample absorption unit 150 may be disposed on the side of the second measurement zone 130. In an embodiment of the present invention, the sample absorption unit 150 may include, but is not limited to, an absorbent pad.

The cassette 10 may further comprise an optical window 160 from which light received from an external optical sensor is reflected. At this time, it is preferable that the external optical sensor is located at the device for measuring glycated hemoglobin ratio, into which the reaction cassette 10 is inserted.

Thereafter, the method for measuring glycated hemoglobin ratio according to the present invention using the cassette for measuring glycated hemoglobin ratio 10 will be described in detail with reference to FIG. 2.

Figure 2:
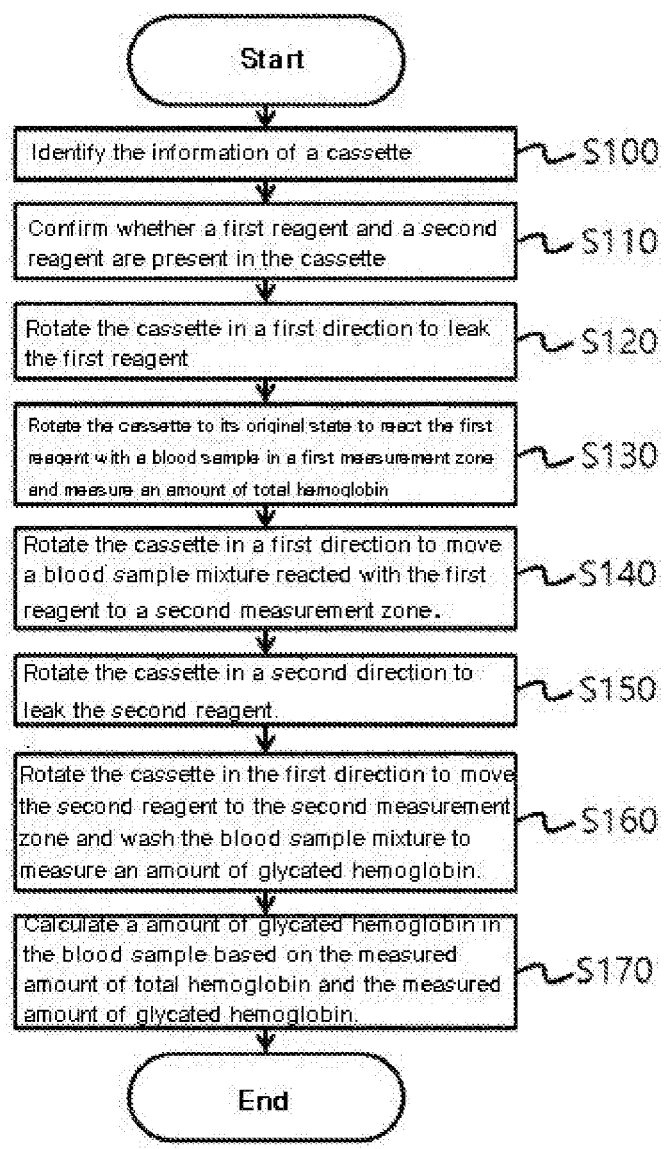
FIG. 2 is a flowchart illustrating the method for measuring glycated hemoglobin ratio according to present invention.

FIG. 2 is a flowchart illustrating the method for measuring glycated hemoglobin ratio using the cassette 10. As shown in FIG. 2, a device for measuring glycated hemoglobin ratio 30 identifies the information of the cassette 10 engaged therein (S100).

Then, the device for measuring glycated hemoglobin ratio 30 confirms whether the first reagent and the second reagent are present in the cassette 10 (S110). This can be confirmed by the cassette 10 check sensor 312.

The blood sample collected from the human body may inject directly into the cassette 10 from outside or may be injected through the blood sampling unit 200 according to an embodiment of the present invention, but is not limited thereto.

Then, the device for measuring glycated hemoglobin ratio 30 rotates the cassette 10 in a first direction to leak the first reagent from the first storage zone 210 (S120).

Next, the cassette 10 rotates to its original state, red blood cells in the blood sample are hemolyzed with the first reagent in the first measurement zone 120, and the amount of total hemoglobin is measured, and then the cassette 10 is vibrated to react the first reagent with the glycated hemoglobin (S130). The blood sample and the first reagent react to form a blood sample mixture accordingly. Here, the cassette 10 may be vibrated or shaken clockwise and counterclockwise for a predetermined period of time, for example, about one minute, so that the hemolyzed blood sample can sufficiently react with the glycated hemoglobin binding material-bead. This is to induce a blood sample of the blood sampling unit 200 to be hemolyzed out by the first reagent and simultaneously to specifically react with the glycated hemoglobin binding material-bead. When the amount of total hemoglobin in the blood sample is measured, it is preferable to measure the amount of total hemoglobin in the blood sample by the optical reflectometry technique through the optical sensor. Also, the cassette 10 may rotate about 1-5° so that the blood sample mixture can gather close to the first measurement zone 120 during the measurement.

Then, when the device for measuring glycated hemoglobin ratio 30 rotates the cassette 10 in the first direction, the blood sample is mixed with the first reagent in the first measurement zone 120, the amount of total hemoglobin is measured, and the blood sample mixture which has been reacted with the first reagent moves to the second measurement zone 130 (S140). Non-glycated hemoglobin and the remaining materials, except for the glycated hemoglobin binding material-bead conjugated with glycated hemoglobin, present in the second measurement zone 130 can be absorbed into the sample absorption unit 150.

Then, the device for measuring glycated hemoglobin ratio 30 rotates the cassette 10 in a second direction to leak the second reagent from the second storage zone 220 (S150).

Then, the device for measuring glycated hemoglobin ratio 30 rotates the cassette 10 in a first direction to move the leaked second reagent to the second measurement zone 130 and washing the blood sample mixture with the second reagent to measure the amount of glycated hemoglobin (S160). Here, as the second reagent containing the washing solution washes the blood sample mixture, non-glycated hemoglobin ($A_o$) non-specifically present in the blood sample may be removed and absorbed into the sample absorption unit 150 together with the second reagent. As in the case of measuring the amount of total hemoglobin from the blood sample mixture reacted with the first reagent, the amount of glycated hemoglobin in the blood sample may be measured by the optical reflectometry technique through the optical sensor.

Then, glycated hemoglobin ratio in the blood sample is calculated by dividing the measured amount of glycated hemoglobin by the measured amount of total hemoglobin (S170). At this time, the glycated hemoglobin ratio is calculated by the following Equation 1.

$$\text{Glycated Hemoglobin Ratio}(\%) = \text{Glycated Hemoglobin}/\text{Total Hemoglobin} \times 100 \quad \text{[Equation 1]}$$

In an embodiment of the present invention, the cassette may rotate 60-130° in the first direction in step a), rotates 60-130° in the second direction in step b), rotates 60-130° in the first direction in step c), rotates 150-240° in the second direction in step d), and rotates 150-220° in the first direction in step e).

Preferably, the cassette may rotate 60-110° in the first direction in step a), rotates 60-110° in the second direction in step b), rotates 80-120° in the first direction in step c), rotates 180-220° in the second direction in step d), and rotates 170-210° in the first direction in step e).

More preferably, the cassette may rotate 80-100° in the first direction in step a), rotates 80-100° in the second direction in step b), rotates 90-110° in the first direction in step c), rotates 180-200° in the second direction in step d), and rotates 180-200° in the first direction in step e).

The range of the rotation angle may be any range as long as the first reagent or the second reagent leaks and moves within an effective range and the amount of hemoglobin can be measured, and is not necessarily limited to the range.

FIG. 3 illustrates (a) an external appearance and (b) an internal appearance according to an embodiment of the cassette 10 which can be used in the method for measuring glycated hemoglobin ratio according to the present invention. The cassette 10 may be used to measure the amount of glycated hemoglobin (HbA1c) in the blood. At this time, the cartridge 20 can be inserted into the cassette 10, and the cassette 10 is engaged in the device for measuring glycated hemoglobin ratio 30 to be rotatable clockwise or counterclockwise with respect to a horizontal axis. The cassette 10 comprises the removing part 100 in the inlet port for the cartridge 20 insertion so that the leakage preventing unit of the cartridge 20 can be caught and removed when the cartridge 20 is inserted into the device. In addition, the cassette 10 comprises in the interior the insertion guide unit 110 for guiding the cartridge 20 to be inserted into the cassette 10 only in one direction. The cassette 10 further comprises on the bottom of the interior a first measurement zone 120 in which the first reagent reacts with the blood sample and the amount of total hemoglobin is measured, and in the middle of the right side a second measurement zone 130 in which the second reagent washes the reacted blood sample and the amount of glycated hemoglobin is measured. The cassette 10 further comprises on the right side the sample absorption unit 150 which absorbs non-glycated hemoglobin and the remaining materials except for the glycated hemoglobin binding material-bead conjugated with glycated hemoglobin. The cassette 10 further comprises on the exterior an optical window 160 from which light received through an external optical sensor is reflected.

Figure 4:
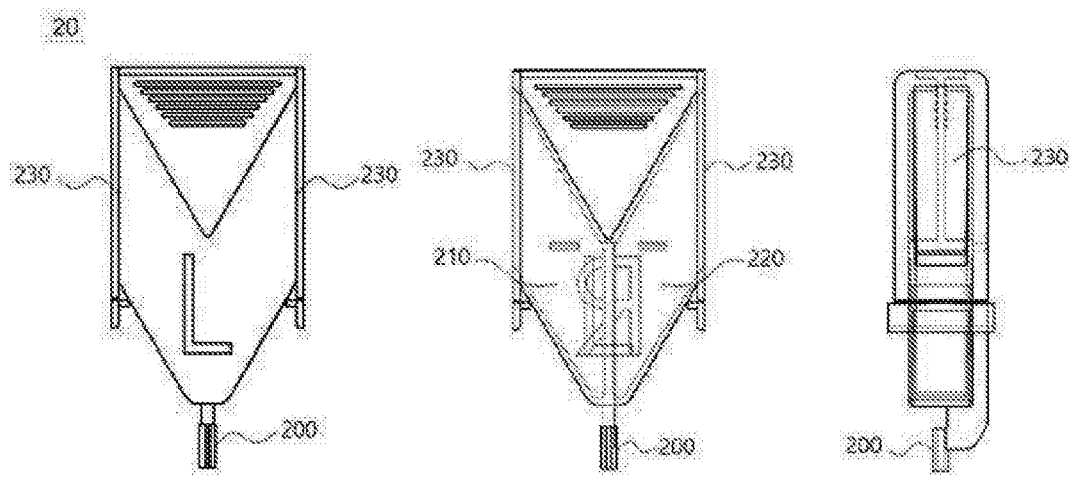
FIG. 4(a), FIG. 4(b), and FIG. 4(c) illustrate a front view, a rear view, and a side view of the external appearance according to an embodiment of the cassette used in the method of the present invention.

FIG. 4 illustrates (a) a front view, (b) a rear view, and (c) a side view of the external appearance of the cartridge 20 which can be used in the method for measuring glycated hemoglobin ratio according to the present invention. The cartridge 20 comprises a first storage zone 210 for storing a first reagent, a second storage zone 220 for storing a second reagent, a blood sampling unit 200 for collecting, containing and leaking a blood sample, a leakage preventing unit 230 for preventing the first reagent and the second reagent from leaking out until the cartridge 20 is inserted into the cassette 10. The leakage preventing unit 230 is formed on upper side of the cartridge 20, respectively. Since the cartridge 20 has a standing rhombus, even if the leakage preventing unit 230 is removed, the first reagent and the second reagent may be accumulated at the bottom of the cartridge 20 in the rhombus shape. Thus, as long as the cartridge 20 is in its original state without rotating, the reagents do not leak from the storage zones. The leakage preventing unit 230 may be a foil cover or a foil tab.

Figure 5A:
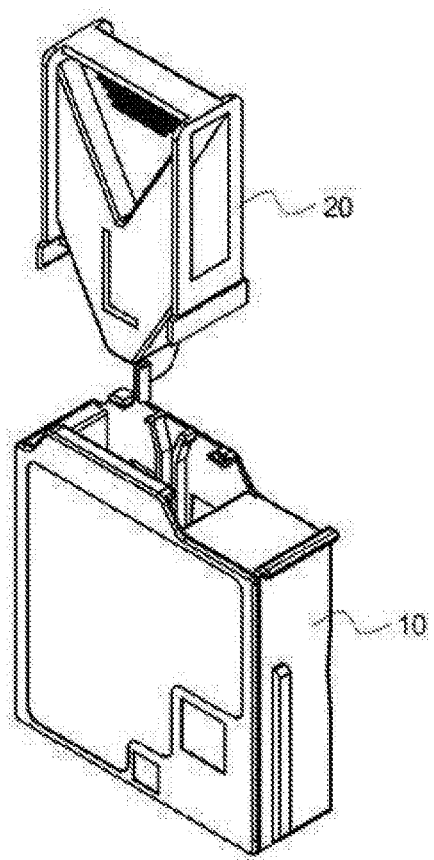
FIG. 5(a) and FIG. 5(b) illustrate the external appearance before and after the cartridge used in the method of the present invention is inserted into the cassette.
Figure 5B:
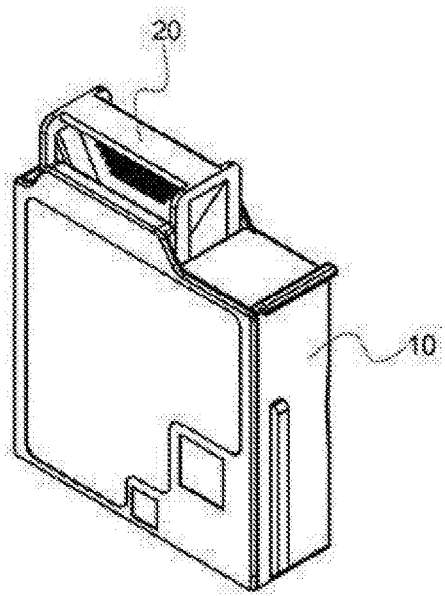

FIG. 5 illustrates the state (a) before and (b) after the cartridge 20 is inserted into the cassette 10. An insertion preventing unit is formed in the cassette 10 so that the cartridge 20 can be inserted only in one direction and the leakage preventing unit 230 of the cartridge 20 can be removed by the removing part 100 of the cartridge 20 at the time of insertion.

Hereinafter, a measuring process of glycated hemoglobin according to the rotation of the cassette 10 into which the cartridge 20 is inserted will be described with reference to FIGS. 6 to 12.

FIG. 6 shows a ready state of the cassette 10 including the first reagent, the second reagent, and the blood sample before rotation. The cartridge 20 is inserted into the cassette 10, the first reagent is contained in the first storage region 210 of the cartridge 20, and the second reagent is contained in the second storage region 220. The leakage preventing unit 230 is caught and removed by removing part 100 when the cartridge 20 is inserted into the cassette 10, and thus is not present. The first reagent and the second reagent do not leak from the storage zones even though the cassette 10 is in its original state without a rotation angle and the leakage preventing unit 230 is not present. Before starting the measurement, the cassette 10 may be shaken for about 30 seconds to allow the reagents in the cassette 10 to mix well.

In advance, as shown in FIG. 7, the cassette 10 may rotate clockwise by about 90°, whereby the first reagent contained in the first storage zone 210 may leak from the leak hole of the first storage zone 210 by gravity. At this time, the second reagent does not leak through the second storage zone 220.

Next, as shown in FIG. 8, when the cassette 10 rotates counterclockwise by about 90° to be in its original state, the first reagent moves to the first measurement zone 120 by the delivery guide unit 140. At this time, the blood sample, which is collected from the human body and contained in the blood sampling unit 200, leaks out through the end of the blood sampling unit 200 to react with the first reagent in the first measuring zone 120. In particular, the cassette 10 can be shaken for about 1 minute using device for measuring glycated hemoglobin 30 so that the reaction of the blood sample with the first reagent occurs more easily. At this time, the amount of total hemoglobin in the blood sample can be measured by an optical reflectometry technique through the optical sensor before the reaction is completely finished in the first measurement zone 120.

As shown in FIG. 9, the cassette 10 can rotate clockwise by about 110°, whereby the blood sample reacts with the first reagent in the first measurement zone 120 to measure total hemoglobin, and then the reacted blood sample mixture moves to the second measurement zone 130. At this time, non-glycated hemoglobin and the remaining materials except for the glycated hemoglobin binding material-bead conjugated with glycated hemoglobin, present in the second measurement zone 130 can be absorbed into the sample absorption unit 150.

As shown in FIG. 10, when the cassette 10 rotates counterclockwise again by about 200°, it is in a state rotated counterclockwise by about 90° based on its original state, whereby the second reagent may leak through the leak hole of the second storage zone 220 by gravity.

Thereafter, when the cassette 10 rotates clockwise again by about 90° as shown in FIG. 11, and then rotates clockwise by about 90° as shown in FIG. 12, the second reagent moves along the delivery guide unit 140 to the second measurement zone 130 in which the blood sample mixture is present. Next, when the second reagent and the blood sample react, i.e., the second reagent washes the blood sample mixture, the amount of the glycated hemoglobin can be measured from the blood sample mixture from which the non-glycated hemoglobin has been removed. At this time, the amount of glycated hemoglobin in the blood sample may be measured by an optical reflectometry technique through the optical sensor. Non-glycated hemoglobin and the remaining materials except for the glycated hemoglobin binding material-bead conjugated with glycated hemoglobin, present in the second measurement zone 130 can be absorbed into the sample absorption unit 150.

In summary, as shown in FIGS. 6 to 12, the device for measuring glycated hemoglobin ratio 30 can automatically rotate the cassette 10 clockwise or counterclockwise. That is, the first reagent or the second reagent leaks sequentially from the first storage zone 210 or the second storage zone 220 according to the rotation of the cassette 10 to react with the blood sample. That is, at least one reagent automatically reacts with the blood sample according to the rotation. In addition, FIGS. 6 to 12 are one example showing the rotation process of the cassette 10 and various other rotations can be embodied. In the case of the embodiments in which each zone of the cassette 10 is positioned symmetrically compared to the above-described embodiments, the cassette 10 can rotate in a manner opposite to the above-described rotation process.

The present invention has been described with reference to the preferred embodiments. However, it will be understood by those skilled in the art that various changes and modifications may be made in the present invention without departing from the spirit or scope of the present invention. Accordingly, the disclosed embodiments should be considered as being exemplary and not limiting. The scope of the present invention is defined in the claims rather than the detailed description, and all differences within the equivalent range should be interpreted as being included in the invention.

DESCRIPTION OF SYMBOLS

| | |
|---|---|
| 10: Cassette | 20: Cartridge |
| 30: Device for measuring glycated hemoglobin ration | 100: Removing part |
| 110: Insertion guide unit | 120: First measurement zone |
| 130: Second measurement zone | 140: Delivery guide unit |
| 150: Sample absorption unit | 160: Optical window |
| 200: Blood sampling unit | 210: First storage zone |
| 220: Second storage zone | 230: Leakage preventing unit |
| 300: Cassette accommodation part | 312: Cassette check sensor |
| 314: Measurement sensor | 320: Driving unit |
| 330: Signal conversion unit | 340: Controller |

The invention claimed is:

1. A method for measuring glycated hemoglobin ratio using a cassette used in a device for measuring glycated hemoglobin ratio,
   wherein the cassette comprises: a cartridge which includes a first storage zone for storing a first reagent, a second storage zone for storing a second reagent, and a blood sampling unit capable of injecting a blood sample into the cassette, and is inserted into the cassette; a first measurement zone in which blood sample introduced from the blood sampling unit reacts with the first reagent to measure an amount of total hemoglobin; and a second measurement zone in which the reacted blood sample reacts with the second reagent to measure an amount of glycated hemoglobin,
   wherein as the cassette rotates by a predetermined angle or more, the first reagent or the second reagent leaks from the first storage zone or the second storage zone, respectively, or moves into the first measurement zone or the second measurement zone, and
   wherein the method comprises the steps of:
   a) rotating the cassette 60-130° in a first direction to leak the first reagent from the first storage zone;
   b) rotating the cassette 60-130° in a second direction to move the leaked first reagent to contact and react the first reagent with the blood sample in the first measurement zone and measuring an amount of total hemoglobin;
   c) rotating the cassette 60-130° in the first direction to move a blood sample mixture formed by reacting the first reagent with the blood sample from the first measurement zone to the second measurement zone;
   d) rotating the cassette 150-240° in the second direction to leak the second reagent from the second storage zone to the second measurement zone;
   e) rotating the cassette 150-220° in the first direction to move the leaked second reagent to the second measurement zone and measuring an amount of glycated hemoglobin in the blood sample mixture; and
   f) dividing the measured amount of glycated hemoglobin by the measured amount of total hemoglobin to calculate glycated hemoglobin ratio in the blood sample,
   wherein the second direction of the steps b) and d) is opposite to the first direction of the steps a), c), and e).

2. The method for measuring glycated hemoglobin ratio according to claim 1, wherein the method further comprises, prior to step a), the steps of:
   1) the reading identification information of the cassette; and
   2) confirming whether the first reagent and the second reagent are present in the cassette.

3. The method for measuring glycated hemoglobin ratio according to claim 1, wherein the first reagent includes a reagent which lyses blood cells in the blood sample and a glycated hemoglobin binding material-bead which selectively reacts with the glycated hemoglobin, wherein the bead includes one or more selected from the group consisting of an agarose bead, a sepharose bead, a latex bead, a glass bead, and a magnetic bead.

4. The method for measuring glycated hemoglobin ratio according to claim 3, wherein the glycated hemoglobin binding material includes one or more selected from the group consisting of a boronic acid, concanavalin A, and an antibody.

5. The method for measuring glycated hemoglobin ratio according to claim 1, wherein the second reagent does not leak from the second storage zone in steps a) to c).

6. The method for measuring glycated hemoglobin ratio according to claim 1, wherein step b) comprises a step of shaking the cassette to facilitate the reaction of the blood sample with the first reagent.

7. The method for measuring glycated hemoglobin ratio according to claim 1, wherein step b) comprises the step of measuring the amount of total hemoglobin in the blood sample by an optical reflectometry technique through an optical sensor.

8. The method for measuring glycated hemoglobin ratio according to claim 1,
   wherein step e) comprises the steps of:
   e1) rotating the cassette in the first direction to move the second reagent to the second measurement zone; and e2) washing the blood sample mixture with the second reagent moved to the second measurement zone to remove non-specific hemoglobin and measuring the amount of glycated hemoglobin in the blood sample.

9. The method for measuring glycated hemoglobin ratio according to claim 1, wherein step e) comprises the step of measuring the amount of glycated hemoglobin in the blood sample by an optical reflectometry technique through an optical sensor.

* * * * *